US005739378A

United States Patent [19]
Jenkins et al.

[11] Patent Number: 5,739,378
[45] Date of Patent: Apr. 14, 1998

[54] COMPLEX HYDROPHOBE-CONTAINING OLIGOMERS

[75] Inventors: Richard Duane Jenkins, Hurricane; David Robinson Bassett, Charleston, both of W. Va.; Gregory Dean Shay, Cary, N.C.

[73] Assignee: Union Carbide Chemicals & Plastics Technology Corporation, Danbury, Conn.

[21] Appl. No.: 887,646

[22] Filed: May 29, 1992

[51] Int. Cl.$^6$ ............................................. C07C 69/73
[52] U.S. Cl. ............................ 560/181; 556/437; 560/199; 564/123
[58] Field of Search ............................ 560/181, 198, 560/199, 205

[56] References Cited

U.S. PATENT DOCUMENTS

| | | | |
|---|---|---|---|
| Re. 33,156 | 1/1990 | Shay et al. | 526/301 |
| 3,035,004 | 5/1962 | Glavis . | |
| 3,190,925 | 6/1965 | Stowe . | |
| 3,277,157 | 10/1966 | Stewart et al. . | |
| 3,341,627 | 9/1967 | Wilkinson . | |
| 3,499,876 | 3/1970 | Field et al. . | |
| 3,652,497 | 3/1972 | Junas et al. . | |
| 3,657,175 | 4/1972 | Zimmerman . | |
| 3,794,608 | 2/1974 | Evani et al. . | |
| 3,894,980 | 7/1975 | DeTommaso . | |
| 3,896,161 | 7/1975 | Borden et al. . | |
| 3,915,921 | 10/1975 | Schlatzer, Jr. . | |
| 3,940,351 | 2/1976 | Schlatzer, Jr. . | |
| 3,960,935 | 6/1976 | Semour . | |
| 4,008,202 | 2/1977 | Evani et al. . | |
| 4,075,411 | 2/1978 | Dickstein | 560/224 |
| 4,079,028 | 3/1978 | Emmons et al. . | |
| 4,085,167 | 4/1978 | Lewis et al. . | |
| 4,128,520 | 12/1978 | Barabas et al. . | |
| 4,138,381 | 2/1979 | Chang et al. . | |
| 4,155,892 | 5/1979 | Emmons et al. . | |
| 4,167,502 | 9/1979 | Lewis et al. . | |
| 4,226,754 | 10/1980 | Yun et al. . | |
| 4,228,277 | 10/1980 | Landoll | 536/90 |
| 4,230,844 | 10/1980 | Chang et al. | 526/210 |
| 4,268,641 | 5/1981 | Koenig et al. | 525/367 |
| 4,338,239 | 7/1982 | Dammann | 524/549 |
| 4,384,096 | 5/1983 | Sonnabend | 526/313 |
| 4,395,524 | 7/1983 | Emmons et al. | 526/307.2 |
| 4,421,902 | 12/1983 | Chang et al. | 526/317 |
| 4,423,199 | 12/1983 | Chang et al. | 526/307.6 |
| 4,426,485 | 1/1984 | Hoy et al. | 524/591 |
| 4,429,097 | 1/1984 | Chang et al. | 526/317 |
| 4,463,151 | 7/1984 | Schutz et al. | 526/307.5 |
| 4,464,524 | 8/1984 | Karickhoff | 526/313 |
| 4,485,209 | 11/1984 | Fan et al. | 524/801 |
| 4,496,708 | 1/1985 | Dehm et al. | 528/76 |
| 4,509,949 | 4/1985 | Huang et al. | 586/558 |
| 4,514,552 | 4/1985 | Shay et al. | 526/301 |
| 4,569,965 | 2/1986 | Engel et al. | 524/544 |
| 4,600,761 | 7/1986 | Ruffner et al. | 526/270 |
| 4,616,074 | 10/1986 | Ruffner | 526/318 |
| 4,703,080 | 10/1987 | Shay et al. | 524/555 |
| 4,722,962 | 2/1988 | Shay et al. | 524/548 |
| 4,735,981 | 4/1988 | Rich et al. | 524/247 |
| 4,764,554 | 8/1988 | Tonge | 524/558 |
| 4,801,671 | 1/1989 | Shay et al. | 526/214 |
| 4,916,183 | 4/1990 | Barron et al. | 524/555 |
| 4,939,283 | 7/1990 | Yokota et al. | 558/33 |
| 5,006,596 | 4/1991 | Chen et al. | 524/555 |
| 5,015,711 | 5/1991 | Simonet et al. | 526/301 |
| 5,023,309 | 6/1991 | Kruse et al. | 528/49 |

FOREIGN PATENT DOCUMENTS 2745872 10/1979 Germany ................. C09B 76/00

OTHER PUBLICATIONS

Morrison et al., Organic Chemistry, Fourth Edition, p. 43 (1983).
The Van Nostrand Chemist's Dictionary, p. 363 (1953).
McGraw–Hill Dictionary of Scientific and Technical Terms, Second Edition, (1978).
Jenkins, R.D. et al., Associative Polymers with Novel Hydrophobe Structures, ACS Meeting, New York, New York, Aug. 26, 1991.
Nemoto, H. et al., J. Org. Chem., 1992, 57, 435.
U.S. Patent Application Serial No. 07/304,258 (D–15741), filed Jan. 31, 1989.

*Primary Examiner*—Christopher Henderson
*Attorney, Agent, or Firm*—W. K. Volles; K. D. Tremain

[57] ABSTRACT

This invention relates to polymers, especially emulsion polymers, and their use for the thickening of a variety of aqueous systems, to methods of thickening utilizing the polymers, to enhancement of such thickening by the addition of surfactants, solvents or non-solvents, and to other aspects including coating compositions and other aqueous systems thickened with the polymers. This invention also relates to new complex hydrophobe-containing oligomers and their use in producing the polymers of this invention.

8 Claims, No Drawings

COMPLEX HYDROPHOBE-CONTAINING OLIGOMERS

RELATED APPLICATIONS

The following are related, commonly assigned applications, filed on an even date herewith: U.S. patent application Ser. No. 07/887,645; U.S. patent application Ser. No. 07/887,647; U.S. patent application Ser. No. 07/887,642; U.S. patent application Ser. No. 07/887,673; U.S. patent application Ser. No. 07/887,672; U.S. patent application Ser. No. 07/887,641; U.S. patent application Ser. No. 07/887,648; U.S. patent application Ser. No. 07/887,643; U.S. patent application Ser. No. 07/887,644; and U.S. patent application Ser. No. 07/877,671; all of which are incorporated herein by reference.

BRIEF SUMMARY OF THE INVENTION

TECHNICAL FIELD

This invention relates to polymers which contain complex hydrophobe-containing oligomers and which can contain nonionic, cationic, anionic and/or amphoteric monomers. The polymers are especially useful as thickeners for aqueous systems.

BACKGROUND OF THE INVENTION

Thickeners for aqueous systems are needed for various purposes, such as for architectual coatings, industrial coatings, automotive coatings and the like to improve rheology of the coatings. Hydroxyethyl cellulose is a well known thickener for aqueous systems, but it has various deficiencies in that excessive amounts must be used and the rheology of the thickened system is inadequate. Various ethoxylated carboxyl-functional polymers which form alkali soluble thickeners are also known, but these have various deficiencies, including inadequate hydrolytic stability.

It has long been desired to provide superior thickeners for aqueous systems which are highly efficient, which better resist hydrolysis, and which provide better rheology. This is achieved herein by providing new polymers which possess these desired characteristics.

DISCLOSURE OF THE THE INVENTION

This invention relates in part to complex hydrophobe-containing oligomers represented by the formula:

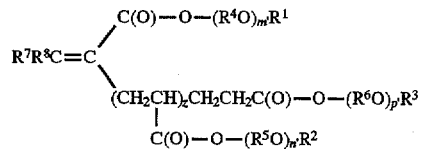

wherein:

$R^1$, $R^2$ and $R^3$ are the same or different and are hydrogen, a substituted or unsubstituted monovalent hydrocarbon residue or a monovalent residue of a substituted or unsubstituted complex hydrophobe compound, provided at least one of $R^1$, $R^2$ and $R^3$ is a monovalent residue of a substituted or unsubstituted complex hydrophobe compound;

m', n' and p' are the same or different and are a value of 0 or greater, preferably a number having an average value of up to 60 or more, provided that at least one of m', n', or p' is a value of at least 2;

z is a value of 0 or greater, preferably a value of from 1 to 5;

each $R^4$ is the same or different and is a substituted or unsubstituted divalent hydrocarbon residue;

each $R^5$ is the same or different and is a substituted or unsubstituted divalent hydrocarbon residue;

each $R^6$ is the same or different and is a substituted or unsubstituted divalent hydrocarbon residue; and $R^7$ and $R^8$ are the same or different and are hydrogen or a substituted or unsubstituted monovalent hydrocarbon residue.

This invention relates-in part to polymers comprising:

(A) about 0–99.9, preferably about 10–70, weight percent of one or more nonionic, cationic, anionic or amphoteric monomers, preferably one or more alpha, beta-monoethylenically unsaturated carboxylic acids, typically methacrylic acid;

(B) about 0–99.9, preferably about 30–85, weight percent of one or more monoethylenically unsaturated monomers, typically ethyl acrylate;

(C) about 0.1–100, preferably about 5–60, weight percent of one or more complex hydrophobe-containing oligomers; and (D) about 0–20, preferably about 0–10, weight percent or greater of one or more polyethylenically unsaturated monomers, typically trimethylol propane triacrylate.

This invention also relates in part to an emulsion of the above-identified polymer in water, which emulsion is useful as a thickening agent in aqueous compositions. In order to obtain the thickening effect, the polymer is dissolved in the aqueous composition to be thickened.

This invention further relates in part to an aqueous composition, and more particularly an improved latex paint composition containing the above-defined polymer.

This invention yet further relates in part to a process for thickening an aqueous composition which comprises adding the above-defined polymer to an aqueous composition and dissolving the polymer in the aqueous composition.

DETAILED DESCRIPTION

Illustrative nonionic, cationic, anionic and amphoteric monomers useful in this invention include those monomers which impart water solubility to the polymer. Preferably, a large proportion of component (A) is employed to impart water solubility to the polymer. The key to water solubility lies in positioning sufficient numbers of hydrophilic functional groups along the backbone or side chains. Suitable functional groups which impart water solubility and suitable nonionic, cationic, anionic and amphoteric monomers useful in this invention are described in Water-Soluble Polymers, Synthesis, Solution Properties and Applications, ACS Symposium Series 467, American Chemical Society (1991), which is incorporated herein by reference. Mixtures of nonionic, cationic, anionic and amphoteric monomers may be employed in this invention, e.g., mixtures of nonionic monomers, mixtures of nonionic and cationic monomers, etc.

Illustrative nonionic monomers useful in this invention include, for example, acrylamide, ethylene oxide, vinyl alcohol, vinyl acetate, N-vinylpyrrolidinone, hydroxyethyl acrylate and the like including mixtures thereof. Illustrative cationic monomers useful in this invention include, for example, ammonium, sulfonium and phosphonium salts, preferably quarternary ammonium salts such as diallyldimethylammonium chloride, diallyldiethylammonium chloride, diethylaminoethyl methacrylate, dimethylaminoethyl methacrylate, methacryloyloxyethyltrimethylammonium sulfate, methacryloyloxyethyltrimethylammonium chloride, 3-(methacrylamido) propyltrimethylammonium chloride and the like including mixtures thereof.

Illustrative anionic monomers useful in this invention include, for example, acrylic acid, methacrylic acid, maleic anhydride, p-styrene carboxylic acids, p-styrene sulfonic acids, vinyl sulfonic acid, 2-acrylamido-2-methylpropane sulfonic acid, 3-acrylamido-3-methylbutanoic acid and the like including mixtures thereof. Illustrative amphoteric monomers useful in this invention contain zwitterions on the same monomers, i.e., betaines, or along the same polymer backbone, i.e., ampholytes, and include, for example, 3-(2-acrylamido-2-methylpropyldimethylammonio)-1-propanesulfonate, N-vinylpyrrolidone-co-N,N-dimethyl-N-methacroyloxyethylammoniopropanesulfonate, N-vinylpyrrolidone co-N,N-dimethyl-N-methacroylamidopropylammoniopropanesulfonate, N-vinylpyrrolidone-co-2-vinylpyridiniopropanesulfonate and the like including mixtures thereof.

A large proportion of one or more alpha, beta-monoethylenically unsaturated carboxylic acid monomers can preferably be present in the polymers of this invention. Various carboxylic acid monomers can be used, such as acrylic acid, methacrylic acid, ethacrylic acid, alpha-chloroacrylic acid, crotonic acid, fumaric acid, citraconic acid, mesaconic acid, itaconic acid, maleic acid and the like including mixtures thereof. Methacrylic acid is preferred. A large proportion of carboxylic acid monomer is essential to provide a polymeric structure which will solubilize and provide a thickener when reacted with an alkali like sodium hydroxide.

The polymers of this invention can also contain a significant proportion of one or more monoethylenically unsaturated monomers. The preferred monomers provide water-insoluble polymers when homopolymerized and are illustrated by acrylate and methacrylate esters, such as ethyl acrylate, butyl acrylate or the corresponding methacrylate. Other monomers which can be used are styrene, alkyl styrenes, vinyl toluene, vinyl acetate, vinyl alcohol, acrylonitrile, vinylidene chloride, vinyl ketones and the like. Nonreactive monomers are preferred, those being monomers in which the single ethylenic group is the only group reactive under the conditions of polymerization. However, monomers which include groups reactive under baking conditions or with divalent metal ions such as zinc oxide may be used in some situations, like hydroxyethyl acrylate.

Other illustrative monoethylenically unsaturated monomers useful in this invention include, for example, propyl methacrylate, isopropyl methacrylate, butyl methacrylate, n-amyl methacrylate, sec-amyl methacrylate, hexyl methacrylate, lauryl methacrylate, stearyl methacrylate, ethyl hexyl methacrylate, crotyl methacrylate, cinnamyl methacrylate, oleyl methacrylate, ricinoleyl methacrylate, hydroxy ethyl methacrylate, hydroxy propyl methacrylate, vinyl propionate, vinyl butyrate, vinyl tert-butyrate, vinyl caprate, vinyl stearate, vinyl laureate, vinyl oleate, vinyl methyl ether, vinyl ethyl ether, vinyl n-propyl ether, vinyl iso-propyl ether, vinyl n-butyl ether, vinyl iso-butyl ether, vinyl iso-octyl ether, vinyl phenyl ether, β-chlorovinyl phenyl ether, vinyl β-naphthyl ether, methacryonitrile, acrylamide, methacrylamide, N-alkyl acrylamides, N-aryl acrylamides, N-vinyl pyrrolidone, N-vinyl-3-morpholinones, N-vinyl-oxazolidone, N-vinyl-imidazole and the like including mixtures thereof.

The complex hydrophobe-containing oligomers of this invention can be prepared by conventional processes such as described in U.S. Pat. No. 4,429,097 by incorporating a complex hydrophobe in place of a conventional hydrophobe.

Illustrative substituted and unsubstituted divalent hydrocarbon residues represented by $R^4$, $R^5$ and $R^6$ in the formula above include those described for the same type of substituents in formulae (i) and (ii) below. Illustrative substituted and unsubstituted monovalent hydrocarbon residues represented by $R^1$, $R^2$, $R^3$, $R^7$ and $R^8$ in the formula above include those described for the same type of substituents in formulae (i) and (ii) below.

The oxyalkylene moieties included in the complex hydrophobe-containing oligomers may be homopolymers or block or random copolymers of straight or branched alkylene oxides. Mixtures of alkylene oxides such as ethylene oxide and propylene oxide may be employed. It is understood that each $R^4$, $R^5$ and $R^6$ group in a particular substituent for all positive values of m', n' and p' can be the same or different.

The complex hydrophobe compounds having at least one active hydrogen useful in preparing the complex hydrophobe-containing oligomers of this invention can be represented by the formula:

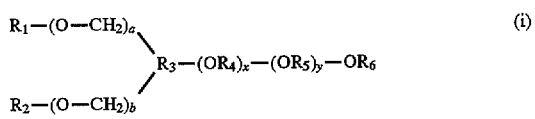

(i)

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$.

Other complex hydrophobe compounds having at least one active hydrogen useful in preparing the complex hydrophobe-containing oligomers of this invention can be represented by the formula:

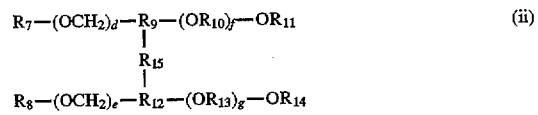

(ii)

wherein $R_7$ and $R_8$ are the same or different and are hydrogen or a substituted or unsubstituted monovalent hydrocarbon residue, $R_{11}$ and $R_{14}$ are the same or different and are hydrogen, a substituted or unsubstituted monovalent hydrocarbon residue or an ionic substituent, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ and $R_{14}$ or having greater than 2 pendant carbon atoms in the case of $R_9$, $R_{10}$, $R_{12}$, $R_{13}$ and $R_{15}$.

Illustrative substituted and unsubstituted monovalent hydrocarbon residues contain from 1 to about 50 carbon atoms or greater and are selected from alkyl radicals including linear or branched primary, secondary or tertiary alkyl radicals, such as methyl, ethyl, n-propyl, isopropyl, amyl, sec-amyl, t-amyl, 2-ethylhexyl and the like; aryl radicals such as phenyl, naphthyl and the like; arylalkyl radicals such as benzyl, phenylethyl, tri-phenylmethylethane and the like; alkylaryl radicals such as octylphenyl, nonylphenyl, dodecylphenyl, tolyl, xylyl and the like; and cycloalkyl radicals such as cyclopentyl, cyclohexyl, cyclohexylethyl and the like.

Preferably, the substituted and unsubstituted hydrocarbon residues are selected from alkyl and aryl radicals which contain from about 1 to 30 carbon atoms or greater. More preferably, the alkyl radicals contain from 1 to 18 carbon atoms, while the aryl, arylalkyl, alkylaryl and cycloalkyl radicals preferably contain from 6 to 18 carbon atoms or greater.

In a preferred embodiment of this invention, $R_1$, $R_2$, $R_7$ and $R_8$ can individually be a hydrocarbon radical represented by the formula:

 (iii)

wherein $R_{16}$ and $R_{17}$ are as defined for $R_1$, $R_2$, $R_7$ and $R_8$ above, h and i are the same or different and are a value of 0 or 1, and $R_{18}$ is as defined for $R_3$ above. For compounds represented by formulae (i) and (ii), it is understood that each formula (iii) radical in a given compound may be the same or different and the $R_{16}$ and/or $R_{17}$ groups may themselves be a formula (iii) radical to provide complex hydrophobes Of a dendritic or of a cascading nature as described below. Further, $R_4$, $R_5$, $R_{10}$ and $R_{13}$ can individually be a hydrocarbon radical represented by the formula:

—CH[(OR$_{19}$)$_j$OR$_{20}$]— (iv)

wherein $R_{19}$ is as defined for $R_4$, $R_5$, $R_{10}$ and $R_{13}$ above, $R_{20}$ is as defined for $R_6$, $R_{11}$ and $R_{14}$ above, and j is a value of 0 or greater.

Illustrative ionic substituents for $R_6$, $R_{11}$, $R_{14}$ and $R_{20}$ include cationic and anionic substituents such as sulfates, sulfonates, phosphates and the like. $R_6$, $R_{11}$, $R_{14}$ and $R_{20}$ may preferably be an organic residue containing 1 or more hydroxyls or nitrogen derivatives or epoxides or other reactive groups which may or may not contain unsaturation.

Other illustrative terminal groups which are described by $R_6$, $R_{11}$, $R_{14}$ and $R_{20}$ include, for example, hydrocarbon residues which may contain allylic or vinylic unsaturation, acrylic or mathacrylic functionality, styryl or alpha-methylstyryl functionality, and the like, such as the reaction product between the terminal alcohol ($R_6$, $R_{11}$, $R_{14}$ and $R_{20}$ =H) and glycidyl methacrylate, isocyanatoethyl methacrylate, alpha, alpha-dimethyl-m-isopropenyl benzyl isocyanate (m-TMI), and the like. Other examples of terminal groups may include hydrocarbon residues of alkyl, aryl, aralkyl, alkaryl, and cycloalkyl radicals which may or may not be substituted with one or more of the following:

hydroxyl, carboxyl, isocyanato, amino, mono- or disubstituted amino, quaternary ammonium, sulfate, sulfonate, phosphate, epoxy, and the like Also included can be divalent siloxy radicals. Other nonhydrocarbon terminal groups may include sulfates, phosphates, and the like.

Illustrative divalent hydrocarbon residues represented by $R_3$, $R_4$, $R_5$, $R_9$, $R_{10}$, $R_{12}$, $R_{13}$, $R_{15}$, $R_{18}$ and $R_{19}$ in the above formulae include substituted and unsubstituted radicals selected from alkylene, -alkylene-oxy-alkylene-, -arylene-oxy-arylene-, arylene, alicyclic radicals, phenylene, naphthylene, -phenylene-(CH$_2$)$_m$(Q)$_n$(CH$_2$)$_m$-phenylene- and -naphthylene-(CH$_2$)$_m$(Q)$_n$(CH$_2$)$_m$-naphthylene-radicals, wherein Q individually represents a substituted or unsubstituted divalent bridging group selected from —CR$_{21}$R$_{22}$—, —O—, —S—, —NR$_{23}$—, —SiR$_{24}$R$_{25}$— and —CO—, wherein $R_{21}$ and $R_{22}$ individually represent a radical selected from hydrogen, alkyl of 1 to 12 carbon atoms, phenyl, tolyl and anisyl; $R_{23}$, $R_{24}$ and $R_{25}$ individually represent a radical selected from hydrogen and methyl, and each m and n individually have a value of 0 or 1. More specific illustrative divalent radicals represented by $R_3$, $R_4$, $R_5$, $R_9$, $R_{10}$, $R_{12}$, $R_{13}$, $R_{15}$, $R_{18}$ and $R_{19}$ include, e.g., 1,1-methylene, 1,2-ethylene, 1,3-propylene, 1,6-hexylene, 1,8-octylene, 1,12-dodecylene, 1,4-phenylene, 1,8-napthylene, 1,1'-biphenyl-2,2'-diyl, 1,1'-binaphthyl-2,2'-diyl, 2,2'-binaphthyl-1,1'-diyl and the like. The alkylene radicals may contain from 2 to 12 carbon atoms or greater, while the arylene radicals may contain from 6 to 18 carbon atoms or greater. Preferably, $R_3$, $R_4$, $R_5$, $R_9$, $R_{10}$, $R_{12}$, $R_{13}$, $R_{15}$, $R_{18}$ and $R_{19}$ are an alkylene or arylene radical.

Illustrative trivalent hydrocarbon residues represented by $R_3$, $R_9$, $R_{12}$ and $R_{18}$ in the above formulae include substituted and unsubstituted radicals selected from

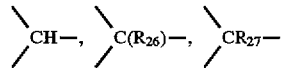

and the like, wherein $R_{26}$ is a substituted or unsubstituted monovalent hydrocarbon residue as described herein and $R_{27}$ is a substituted or unsubstituted divalent hydrocarbon residue as described herein.

Of course, it is to be further understood that the hydrocarbon residues in the above formulae may also be substituted with any permissible substituent. Illustrative substituents include radicals containing from 1 to 18 carbon atoms such as alkyl, aryl, aralkyl, alkaryl and cycloalkyl radicals; alkoxy radicals; silyl radicals such as —Si(R$_{28}$)$_3$ and —Si(OR$_{28}$)$_3$, amino radicals such as —N(R$_{28}$)$_2$; acyl radicals such as —C(O)R$_{28}$; acyloxy radicals such as —OC(O)R$_{28}$; carbonyloxy radicals such as —COOR$_{28}$; amido radicals such as —C(O)N(R$_{28}$)$_2$ and —N(R$_{28}$)COR$_{28}$; sulfonyl radicals such as —SO$_2$R$_{28}$; sulfinyl radicals such as —SO(R$_{28}$)$_2$; thionyl radicals such as —SR$_{28}$; phosphonyl radicals such as —P(O)(R$_{28}$)$_2$; as well as halogen, nitro, cyano, trifluoromethyl and hydroxy radicals and the like, wherein each $R_{28}$ can be a monovalent hydrocarbon radical such as alkyl, aryl, alkaryl, aralkyl and cycloalkyl radicals, with the provisos that in amino substituents such as —N(R$_{28}$)$_2$, each $R_{28}$ taken together can also compromise a divalent bridging group that forms a heterocyclic radical with the nitrogen atom, in amido substituents such as —C(O)N(R$_{28}$)$_2$ and —N(R$_{28}$)COR$_{28}$, each $R_{28}$ bonded to N can also be hydrogen, and in phosphonyl substituents such as —P(O)(R$_{28}$)$_2$, one $R_{28}$ can by hydrogen. It is to be understood that each $R_{28}$ group in a particular substituent may be the same or different. Such hydrocarbon substituent radicals could possibly in turn be substituted with a permissible substituent such as already herein outlined above.

Preferred alkylene oxides which can provide random or block oxyalkylene units in the complex hydrophobe compounds represented by formulae (i) and (ii) include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, 1,2-decylene oxide, and higher alpha-olefin epoxides; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorohydrin and epibromohydrin. The preferred alkylene oxides are ethylene oxide and propylene oxide. Also included can be hydrocarbon residues from substituted and unsubstituted cyclic esters or ethers such as oxetane and tetrahydrofuran. It is understood that the compounds represented by formulae (i) and (ii) herein can contain random and/or block oxyalkylene units as well as mixtures of oxyalkylene units. It is further understood that each $R_4$, $R_5$, $R_{10}$, $R_{13}$ and $R_{19}$ group in a particular substituent for all positive values of x, y, f, g and j respectively can be the same or different.

The values of x, y, f, g, j, m', n' and p' are not narrowly critical and can vary over a wide range. For example, the values of x, y, f, g, j, m', n' and p' can range from 0 to about 200 or greater, preferably from about 0 to about 100 or greater, and more preferably from about 0 to about 50 or greater. Any desired amount of alkylene oxide can be employed, for example, from 0 to about 90 weight percent or greater based on the weight of the complex hydrophobe compound.

Referring to the general formulae (i) and (ii) above, it is appreciated that when $R_1$, $R_2$, $R_7$ and/or $R_8$ are a hydrocarbon residue of formulae (iii) above, the resulting compound may include any permissible number and combination of hydrophobic groups of the dendritic of cascading type. Such compounds included in the above general formulae should be easily ascertainable by one skilled in the art. Illustrative complex hydrophobe compounds having at least one active hydrogen useful in this invention and processes for preparation thereof are disclosed in copending U.S. patent application Ser. No. 07/887,648, incorporated herein by reference.

In a preferred embodiment of this invention, the structure shown in formula (iii) can be a residue of the reaction product between epichlorohydrin and an alcohol, including those alcohols whose residues can be described by formula (iii), or a phenolic, or a mixture thereof. The structures which result can be described as complex hydrophobes of a dendritic or of a cascading nature. Pictorially, they can be described as shown below:

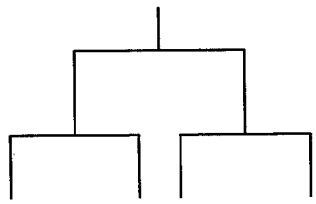

The complex hydrophobe-containing oligomers of useful in this invention can undergo further reaction(s) to afford desired derivatives thereof. Such permissible derivatization reactions can be carried out in accordance with conventional procedures known in the art. Illustrative derivatization reactions include, for example, esterification, etherification, alkoxylation, amination, alkylation, hydrogenation, dehydrogenation, reduction, acylation, condensation, carboxylation, oxidation, silylation and the like, including permissible combinations thereof. This invention is not intended to be limited in any manner by the permissible derivatization reactions or permissible derivatives of complex hydrophobe-containing oligomers.

More particularly, the hydroxyl-terminated complex hydrophobe-containing oligomers of this invention can undergo any of the known reactions of hydroxyl groups illustrative of which are reactions with acyl halides to form esters; with ammonia, a nitrile, or hydrogen cyanide to form amines; with alkyl acid sulfates to form disulfates; with carboxylic acids and acid anhydrides to form esters and polyesters; with alkali metals to form salts; with ketenes to form esters; with acid anhydrides to form carboxylic acids; with oxygen to form aldehydes and carboxylic acids; ring-opening reactions with lactones, tetrahydrofuran; dehydrogenation to form aldehydes, isocyanates to form urethanes, and the like.

The polymers of this invention can be prepared via a variety of polymerization techniques known to those skilled in the art. The technique of polymerization influences the microstructure, monomer sequence distribution in the polymer backbone and its molecular weight to influence the performance of the polymer. Illustrative polymerization techniques include, for example, conventional and staged emulsion polymerization via batch, semi-continuous, or continuous processes, micellar polymerization, inverse emulsion polymerization, solution polymerization, non-aqueous dispersion polymerization, interfacial polymerization, emulsion polymerization, suspension polymerization, precipitation polymerization, addition polymerizations such as free radical, anionic, cationic or metal coordination methods, and the like.

The thickeners of this invention possess structural attributes of two entirely different types of thickeners (those which thicken by pH dependent solubilization of a high molecular weight entity, and those which thicken due to association), and this may account for the superior thickener properties which are obtained herein.

The aqueous emulsion copolymerization is entirely conventional. To obtain an estimate of thickening efficiency, the product can be diluted with water to about 1% solids content and then adjust the pH to solubilize the polymer. The usual alkali is ammonium hydroxide, but sodium and potassium hydroxide, and even amines, like triethylamine, may be used for neutralization. The usual acid is sulfuric acid, acetic acid and the like. After adjustment to appropriate pH, the product dissolves in the water to provide an increase in the viscosity. In the normal mode of addition, the unsolubilized thickener is added to a paint and then the pH is adjusted. This facilitates handling the thickener because it has a lower viscosity before pH adjustment. This procedure also makes more water available for the paint formulation.

The polymers of this invention are preferably produced by conventional aqueous emulsion polymerization techniques, using appropriate emulsifiers for emulsifying the monomers and for maintaining the polymer obtained in a suitable, dispersed condition. Commonly used anionic surfactants such as sodium lauryl sulfate, dodecylbenzene sulfonate and ethoxylated fatty alcohol sulfate can be used as emulsifiers. The emulsifier may be used in a proportion of ½ to 6% of the weight monomers.

Preferably, water-soluble initiators such as alkali metal or ammonium persulfate are used in amounts from 0.01 to 1.0% on the weight of monomers.

A gradual addition thermal process employed at temperatures between 60° C. to 100° C. is preferred over redox systems.

The polymerization system may contain small amounts (0.01 to 5% by weight, based on monomer weight) of the chain transfer agent mercaptans such as hydroxyethyl mercaptan, β-mercaptopropionic acid and alkyl mercaptans containing from about 4 to 22 carbon atoms, and the like. The use of mercaptan modifier reduces the molecular weight of the polymer and therefore its thickening efficiency.

The polymers of this invention may further be modified by introducing an amount of component (D), namely, one or more polyethylenically unsaturated copolymerizable monomers effective for crosslinking, such as diallylphthalate, divinylbenzene, allyl methacrylate, trimethylol propane triacrylate, ethyleneglycol diacrylate or dimethacrylate, 1,6-hexanediol diacrylate or dimethylacrylate, diallyl benzene, and the like. Thus, from about 0.05 or less to about 20% or greater of such polyethylenically unsaturated compound based on total weight of monomer may be included in the composition forming the polymer. The resulting polymers are either highly branched or in the form of three-dimensional networks. In the neutralized salt form, those networks swell in an aqueous system to act as a highly efficient thickener.

Other illustrative polyethylenically unsaturated monomers useful in this invention include, for example, any copolymerizable compound which contains two or more nonconjugated points of ethylenic unsaturation or two or more nonconjugated vinylidene groups of the structure, $CH_2=C=$, such as divinyltoluene, trivinylbenzene, divinylnaphthalene, trimethylene glycol diacrylate or dimethacrylate, 2-ethylhexane-1,3-dimethyacrylate, divinylxylene, divinylethylbenzene, divallyl ether, divinyl sulfone, allyl ethers of polyhydric compounds such as of glycerol, pentaerythritol, sorbitol, sucrose and resorcinol, divinylketone, divinylsulfide, allyl acrylate, diallyl maleate, diallyl fumarate, diallyl phthalate, diallyl succinate, diallyl carbonate, diallyl malonate, diallyl oxalate, diallyl adipate, diallyl sebacate, diallyl tartrate, diallyl silicate, triallyl tricarballylate, triallyl aconitate, triallyl citrate, triallyl phosphate, N,N-methylenediacrylamide, N,N'-methylenedimethacrylamide, N,N'-ethylidenediacrylamide and 1,2-di-(α-methyl-methylenesulfonamide)-ethylene.

The polymer may be utilized in a variety of ways to provide the thickener or thickened compositions of this invention. For example, the polymer, while in aqueous dispersion or dry form, may be blended into an aqueous system to be thickened followed by addition of a pH adjusting agent. Alternatively, the polymer may first be solubilized in aqueous dispersion form and then blended with the aqueous system. Preferably, if co-thickening by a surfactant is desired, the components are separately blended (as dry components or as dispersions or slurries) into an aqueous dispersion to be thickened, followed by the pH adjustment step. Although aqueous concentrates of the polymer in unsolubilized form and the surfactant may be formed and added to an aqueous dispersion to be thickened as needed, followed by pH adjustment, such concentrates tend to be too viscous for easy handling. It is nevertheless possible to prepare either a dry blend or an aqueous, high solids composition which is sufficiently low in viscosity as to be pumpable or pourable, and then to further thicken the admixture by addition of an alkaline or acidic materials.

The polymer thickener may be provided in a dry state in number of ways. For example, the unsolubilized polymer may be spray or drum dried and, if desired, blended with a surfactant co-thickener. However, it is also possible to spray dry or otherwise dehydrate the solubilized polymer thickener, and then reconstitute the aqueous thickener dispersion at a future time and place by agitation in a aqueous medium, provided the pH of the dispersion is maintained at an appropriate value.

The more usual method of application of the dispersion of this invention for aqueous thickening is to add the aqueous dispersion of the polymer to the medium to be thickened and, after mixing, to introduce an alkaline or acidic material to ionize component (A). The major portion of the thickening effect is obtained in a few minutes upon pH adjustment. In the presence of high concentrations of electrolytes, the viscosity development may take much longer. This method of applying a polymer to an aqueous system before pH adjustment enables one to handle a high solids thickener in a non-viscous state, to obtain uniform blend, and then to convert to a highly viscous condition by the simple addition of an alkaline or acidic material to bring the pH of the system to an appropriate value.

An enhancement of thickening (herein termed "co-thickening") can result upon the addition of a surfactant to an aqueous system containing the polymer of this invention, when the polymer is solubilized. In some cases the thickening can be enhanced up to about 40 times the viscosity afforded by the solubilized polymer alone. A wide range of surfactants may be used. Although trace amounts of surfactant may be residually present from the polymerization of the monomers comprising the polymer (for example, whatever may remain of the about 1.5 weight percent surfactant on monomers), such amounts of surfactant are not believed to result in any measurable co-thickening.

On the basis of an aqueous system containing about 0.1 to 5% by weight of polymer solids, a useful amount of surfactant for optimum co-thickening is about 0.1 to 1.0% by weight of the total system. As indicated, the amounts of polymer and surfactant cothickener may vary widely, even outside these ranges, depending on polymer and surfactant type and other components of the aqueous system to be thickened. However, the co-thickening can reach a maximum as surfactant is added and then decreases as more surfactant is added. Hence, it may be uneconomical to employ surfactant in amounts outside the stated concentrations and polymer/surfactant ratios, but this can be determined in a routine manner in each case.

The preferred method of application of the polymer and the surfactant for aqueous thickening is to add in any sequence the polymer and the surfactant to the medium to be thickened and, after mixing, to introduce an alkaline or acidic material to adjust the pH. This method of applying polymer and surfactant to an aqueous system before pH adjustment enables one to handle a high solids thickener in a non-viscous state, to obtain a uniform blend, and then to convert to a highly viscous condition by the simple addition of an alkaline or acidic material to bring the pH of the system to an appropriate value. However, the pH of the aqueous system may also be adjusted before addition of the surfactant.

The surfactants which may be used include nonionics and anionics, singly or in combination, the selection necessarily depending upon compatibility with other ingredients of the thickened or thickenable dispersions of this invention. Cationic and amphoteric surfactants may also be used provided they are compatible with the polymer and other ingredients of the aqueous system, or are used in such small amounts as not to cause incompatibility.

Suitable anionic surfactants that may be used include the higher fatty alcohol sulfates such as the sodium or potassium salt of the sulfates of alcohols having from 8 to 18 carbon atoms, alkali metal salts or amine salts of high fatty acid having 8 to 18 carbon atoms, and sulfonated alkyl aryl compounds such as sodium dodecyl benzene sulfonate. Examples of nonionic surfactants include alkylphenoxy-polyethoxyethanols having alkyl groups of about 7 to 18 carbon atoms and about 9 to 40 or more oxyethylene units such as octylphenoxypolyethoxyethanols, dodecylphenoxy-polyethoxyethanols; ethylene oxide derivatives of long-chain carboxylic acids, such as lauric, myristic, palmitic, oleic; ethylene oxide condensates of long-chain alcohols such as lauryl or cetyl alcohol, and the like.

Examples of cationic surfactants include lauryl pyridinium chloride, octylbenzyltrimethylammonium chloride, dodecyltrimethylammonium chloride condensates of primary fatty amines and ethylene oxide, and the like.

The foregoing and numerous other useful nonionic, anionic, cationic, and amphoteric surfactants are described in the literature, such as McCutcheon's Detergents & Emulsifiers 1981 Annual, North America Edition, MC Publishing Company, Glen Rock, N.J. 07452, U.S.A., incorporated herein by reference.

In general, solvents and non-solvents (or mixtures of solvents, non-solvents, other organics and volatiles) can be used to manipulate the viscosity of polymer containing systems. For example, mineral spirits can act like a co-thickener. The co-thickening with mineral spirits has utility in textile printing pastes, and in waterborne automotive basecoats. These systems usually contain mineral spirits (because of the pigments used therein), so that the mineral spirits provide an economical way of increasing viscosity and improving the efficiency of the thickener.

The amount of the polymer that may be dissolved in any given aqueous composition may fall within a wide range depending on the particular viscosity desired.

Thus, although any effective amount of the polymer may be employed for dissolution, typically from about 0.05 to about 20%, preferably from about 0.1 to about 5%, and most preferably from about 0.1 to about 3% by weight, based on the weight of the final aqueous composition including polymer is used.

For latex paint compositions, the polymer may be dissolved therein in an amount of from about 0.05 to about 5%, and preferably from about 0.1 to about 3% by weight, based on the weight of the total composition including polymer.

The polymers of this invention may be employed as thickeners for controlling viscosity of any aqueous based composition. An aqueous based composition is an aqueous composition as herein defined to be a composition wherein water comprises at least 10% by weight of the total composition (including 100% water).

For example, aqueous dispersions, emulsions, suspensions, solutions, slurries and the like, may be thickened by the polymers of this invention.

Typical aqueous compositions include compositions to be applied to textiles such as latex adhesives, warp sizes, backings for rugs and other pile fabrics. The polymer may also be used when thickening is desired in the purification of raw water such as the saline water used in the recovery of oil from exhausted oil wells by water flooding techniques. Other aqueous coatings compositions to which the polymer can be added for thickening purposes include drilling muds, caulks, adhesives, coating compositions such as paper coatings, furniture finishes, ink compositions, latex paints, foundry core washes, and the like.

Preferably, the polymer is used to thicken aqueous coating compositions, and more preferably latex paint compositions.

Examples of suitable latex paint compositions include those based on resins or binders of acrylonitrile, copolymers of acrylonitrile wherein the comonomer is a diene like isoprene, butadiene or chloroprene, homopolymers of styrene, homopolymers and copolymers of vinyl halide resins such as vinyl chloride, vinylidene chloride or vinyl esters such as vinyl acetate, vinyl acetate homopolymers and copolymers, copolymers of styrene and unsaturated acid anhydrides like maleic anhydrides, homopolymers and copolymers of acrylic and methacrylic acid and their esters and derivatives, polybutadiene, polyisoprene, butyl rubber, natural rubber, ethylene-propylene copolymers, olefins resins like polyethylene and polypropylene, polyvinyl alcohol, carboxylated natural and synthetic latices, epoxies, epoxy esters and similar polymeric latex materials.

Latex paint compositions are well known in the art and typically comprise an emulsion, dispersion or suspension of discrete particles of resin binder and pigment in water. Optional ingredients typically include thickeners, antifoam agents, plasticizers, surfactants, coalescing agents, and the like.

The polymers described herein are useful in a variety of aqueous systems, such as textile coatings (woven and nonwoven), latex paint formulations, cosmetic formulations, pigment dispersions and slurries, dentrifrices, hand lotions, liquid detergents, quenchants, agricultural chemicals, concrete additives, transmission fluids, waste water treatment (flocculants), turbulent drag reduction, aircraft anti-icing, automation coatings (OEM and refinish, architectural coatings, industrial coatings and the like.

As used herein, the term "complex hydrophobe" is contemplated to include all permissible hydrocarbon compounds having 2 or more hydrophobe groups, e.g., bis-dodecylphenyl, bis-nonylphenyl, bis-octylphenyl and the like.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

The invention is illustrated by certain of the following examples.

EXAMPLE 1

Preparation of 1,3-Bis(nonylphenoxy)-2-propanol

To a five neck, two liter round bottom flask equipped with an addition funnel, thermometer, nitrogen dispersant tube, mechanical stirrer, and a decanting head with a water-cooled condenser were added 220 grams (1.00 mole) of nonylphenol and 250 milliliters of cyclohexane. The solution was then heated to reflux and 2.8 grams (1.3 wt. % based on nonylphenol) of potassium hydroxide in 10 milliliters of water was slowly added to the flask. After essentially all the water was recovered in the decanting head (10 milliliters+1 milliliter formed), 250.7 grams (0.91 mole) of nonylphenyl glycidyl ether as added dropwise. During the addition of the glycidyl ether, the reaction temperature was maintained between 60° and 80° C. After the addition was complete, the solution was refluxed for four hours. The contents of the flask were then washed with a five percent aqueous solution of phosphoric acid, and the organic layer was separated from the water layer and washed twice with deionized water. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180°C. during the distillation to prevent discoloration of the product. The concentrated solution was then refiltered to give 425 grams of a pale-yellow liquid. End-group MW analysis gave a molecular weight of 506.8 (theoretical MW=496.8). Ir and nmr spectra were identical to previously recorded spectra for the compound.

EXAMPLE 2

Preparation of 1,3-Bis(nonylphenoxy)-2-propanol

To a five neck, two liter round bottom flask, equipped with an addition funnel, thermometer, nitrogen dispersant tube, mechanical stirrer, and a decanting head with a water-cooled condenser, were added 300 milliliters of cyclohexane and 451.7 grams (2.05 mole) of nonylphenol. The solution was then heated to reflux and 58.9 grams (1.05 mole) of potassium hydroxide in 60 milliliters of water was slowly added via the addition funnel. After essentially all the water was recovered in the decanting head (60 milliliter+19 milliliters formed), the reaction was cooled to 40° C., and 92.5 grams (1.00 mole) of epichlorohydrin was slowly added. During the addition, the reaction temperature was maintained below 60° C. by controlling the rate of epichlorohydrin addition. After all the epichlorohydrin was added, the solution was allowed to stir for one hour, and then brought to reflux for an additional three hours. The reaction mixture was then filtered under vacuum through a steam-jacketed Buchner funnel to remove the potassium chloride formed as a by-product. The filtration process was performed a total of three times to remove the majority of the salts. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180° C. during the distillation to prevent discoloration of the product. The concentrated solution was then refiltered to give 275 grams of a pale-yellow liquid. End-group MW analysis gave a molecular weight of 459.7 (theoretical MW=496.8). Ir and nmr spectra were identical to previously recorded spectra for the compound.

EXAMPLE 3

Preparation of 5 Mole Ethoxylate of 1,3-Bis (nonylphenoxy)-2-propanol

To a 500 milliliter, stainless steel, high pressure autoclave was charged 200 grams (0.40 mole) of 1,3-bis (nonylphenoxy)-2-propanol, which contained a catalytic amount of the potassium salt of the alcohol as described in Example 1. After purging the reactor with nitrogen, the alcohol was heated to 130° C. with stirring, and 86.9 grams (2.0 mole) of ethylene oxide was added over a two hour period. The reaction temperature and pressure were maintained from 130° C. to 140° C. and 60 psig during the course of the reaction. After the addition of ethylene oxide was complete, the reaction mixture was held at 140° C. for an additional hour to allow all the ethylene oxide to cook out.

The reaction mixture was dumped while hot, under nitrogen, and neutralized with acetic acid to yield 285 grams of a pale-yellow liquid.

EXAMPLE 4

Preparation of Adduct of Nonylphenyl Glycidyl Ether and 5 Mole Ethoxylate of 1,3Bis (nonylphenoxy)-2-propanol To a five neck, one liter, round bottom flask equipped as in Example 1 was added 119.8 grams (0.17 mole) of the 5 mole ethoxylate of 1,3-bis(nonylphenoxy)-2-propanol and 100 milliliters of cyclohexane. The mixture was refluxed (100° C.) for one hour to remove residual water, and then cooled to 50° C. under nitrogen to add 0.5 grams of $BF_3/Et_2O$. Nonylphenyl glycidyl ether (46.0 grams, 0.17 mole) was then added to the flask over a one hour period, and the reaction was heated to reflux. After three hours at reflux, the reaction mixture was transferred to a separatory funnel, while hot, and washed with a saturated aqueous solution of sodium bicarbonate. The organic layer was separated from the water layer, and washed twice with hot deionized water. The washes were performed at 50° C. to facilitate the separation of the two layers. The water and cyclohexane were then evaporated from the organic layer, under vacuum, to yield 145 grams of a pale-yellow, viscous liquid. End-group molecular weight analysis gave a molecular weight of 880 (theoretical molecular weight=993).

EXAMPLE 5

Preparation of Poly(nonylphenol glycidyl ether)

To a 500 milliliter round bottom equipped with an overhead stirrer, nitrogen inlet, reflux condenser, additional funnel, and temperature controller was charged 1.9 grams of ethanol (22 mmoles) and 200 grams of cyclohexane. The solution was brought to 50° C. Once heated, 0.5 milliliters (4 mmoles) of $BF_3/Et_2O$ was added using a 2 milliliter syringe. Once the acid was added, 100.0 grams of nonylphenol glycidyl ether (362 mmoles) was added dropwise so as to maintain a reaction temperature of 45° C.–55° C. Once the glycidyl ether was added, the solution is refluxed for 3 hours, then cooled to about 50° C.

While hot (<60° C.) the organic was transferred to a separatory funnel and was washed once with 100 milliliters of 5% sodium bicarbonate solution. The aqueous layer was drained and the organic was washed two more times with 100 milliliter portions of deionized water. The aqueous layers were decanted and the organic was dried for at least 1 hour over magnesium sulfate. Once dry the magnesium sulfate was filtered from the organic which was stripped of solvent using a rotary evaporator. The final yield of viscous polymer was 100 grams. The GPC molecular weight was Mw=2600 and the Mn=1700 based on monodisperse polystyrene standards.

EXAMPLE 6

Ethoxylation of Poly(nonylphenol glycidyl ether)

To a 500 milliliter stainless steel Zipperclave was added 60.0 grams (0.035 moles based on an approximate molecular weight of 1700 gram/mole) of the resin prepared in Example 5 along with 0.5 grams of potassium hydroxide. The vessel was attached to an automated ethoxylation unit and was heated to 50° C. The vessel was continuously purged with nitrogen for 15 minutes and was then heated to 100° C.

where it was again continuously purged with nitrogen for another 15 minutes. The vessel was then heated to 140° C. and was given a series of 6 purges by pressuring the vessel up to 80 psi, and then venting. Once the venting process was complete, the vessel was pressured to 20 psi with nitrogen.

The ethylene oxide lines were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until 60.0 grams of ethylene oxide (1.362 moles) was added based on a difference weight of the feed cylinder. After the feed was complete, the reaction was allowed to continue for 1 hour after which the vessel was cooled to 60° C., purged 4 times with nitrogen to 80 psi and was dumped to a container. The final product yield was 115 grams with a theoretical yield of 120 grams. The GPC molecular weight of the product was Mw=3550 and the MN=2930 based on monodisperse polystyrene standards.

EXAMPLE 7

Preparation of Poly(phenyl glycidyl ether)

To a 500 milliliter round bottom equipped with an overhead stirrer, nitrogen inlet, reflux condenser, addition funnel, and temperature controller was charged 47.06 grams of phenol (500 mmoles) and 100 grams of toluene. The solution was brought to 50° C. Once heated, 1.0 milliliter (8 mmoles) of $BF_3/Et_2O$ was added using a 2 milliliter syringe. Once the acid was added, 68.18 grams of phenyl glycidyl ether (454 mmoles) was added dropwise so as to maintain a reaction temperature of 45° C.–55° C. Once the glycidyl ether was added, the solution is refluxed for 3 hours, then cooled to about 50° C.

While hot (<60° C.) the organic was transferred to a separatory funnel and was washed once with 100 milliliters of 5% sodium bicarbonate solution. The aqueous layer was drained and the organic was washed two more times with 100 milliliter portions of deionized water. The aqueous layers were decanted and the organic was dried for at least 1 hour over magnesium sulfate. Once dry the magnesium sulfate was filtered from the organic which was stripped of solvent using a rotary evaporator. The final yield of viscous polymer was 90.3 grams (with 11% unreacted phenol). The GPC molecmolecular weight was Mw=470 and the Mn=310 (on average a trimer) based on monodisperse polystyrene standards.

EXAMPLE 8

Preparation of 1,3-Bis(phenoxy)-2-propanol using the Cascading Polyol Technique

To a 1 liter round bottom flask equipped with an overhead stirrer, nitrogen inlet, reflux condenser, addition funnel, and temperature controller was charged 94.11 grams of phenol (1 mole), 12.86 grams of tetraethylammonium iodide (0.05 moles), 3.00 grams of water (0.17 moles), 42.08 grams of potassium hydroxide (0.75 moles), and 250 grams of toluene. To a 100 milliliter additional funnel was charged 23.13 grams of epichlorohydrin (0.25 moles) and 50 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliters portions of deionized water. The aqueous layers were drained off, and the toluene was removed along with unreacted phenol using a rotary evaporator. The final yield of product was 64.5 grams which was 106% of theory (residual is phenol). Final product purity was about 95% as shown by GPC.

EXAMPLE 9

Dimerization of 1,3-Bis(phenoxy)-2-propanol using the Cascading Polyol Technique To a 250 milliliter round bottom flask equipped with an overhead stirrer, nitrogen inlet, reflux condenser, additional funnel, and temperature controller was charged 20.03 grams of 1,3-bis-(phenoxy)-2-propanol prepared in Example 8 (82 moles), 2.06 grams of tetraethylammonium iodide (8 mmoles), 0.49 grams of water (27 moles), 6.51 grams of potassium hydroxide (116 mmoles), and 125 grams of toluene. To a 100 milliliter addition funnel was charged 3.61 grams of epichlorohydrin (39 mmoles) and 25 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliter portions of deionized water. The aqueous layers were drained off, and the toluene was removed using a rotary evaporator. The final yield of product was 21.6 grams which was 101% of theory. GPC showed two major components of the product. The first was the starting material at about 41% (Mn=220) and the second was the coupled product at about 59% (Mn=520).

EXAMPLE 10

Preparation of 1,3-Bis(hexadecyloxy)-2-propanol using the Cascading Polyol Technique To a 500 milliliter round bottom flask equipped with an overhead stirrer, nitrogen inlet, reflux condenser, additional funnel, and temperature controller was charged 60.61 grams of hexadecanol (0.25 moles), 6.18 grams of tetraethylammonium iodide (0.024 moles), 1.44 grams of water (0.082 moles), 20.20 grams of potassium hydroxide (0.36 moles), and 125 grams of toluene. To a 100 milliliter addition funnel was charged 11.10 grams of epichlorohydrin (0.12 moles) and 25 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliter portions of deionized water. The aqueous layers were drained off, and the toluene was removed using a rotary evaporator. The final yield of product was 70.9 grams which is 109% of theory (residual is hexadecanol).

EXAMPLE 11

Sulfation of 1,3-Bis(nonylphenoxy)2-propanol-block-(propylene oxide)$_{10}$-block-(ethylene oxide)$_{10}$ To a 250 milliliter round bottom flask equipped with an overhead stirrer, a temperature controller, and a vacuum adapter was added 75.0 grams of the material from Example 13 (49 mmoles). The kettle was then evacuated to <20 mmHg and heated to 100° C. to remove any water. After 1 hour, the kettle was cooled to 60° C. while under vacuum. When reaching 60° C., vacuum was broken with nitrogen and 5.3 grams of sulfamic acid (54 mmoles) was added. After charging the sulfamic acid, the kettle was heated to 110° C. and evacuated to <20 mmHg. The reaction was allowed to proceed for 3 hours.

At the end of the hold period, the kettle was cooled to 85° C. and vacuum was broken with nitrogen. 1.2 grams of diethanolamine (11 mmoles) was slowly added under a blanket of nitrogen. This solution was stirred for 30 minutes. 10 grams of ethanol was added to the kettle and the temperature was regulated to 55° C. This solution was stirred for 30 minutes. The heat was removed from the kettle and 30 grams of water along with 20 grams of ethanol were added while maintaining good agitation. The solution was stirred for 15 minutes or until cooled to room temperature (<35° C.).

The pH was checked by dissolving 2 grass of the product solution in 18 grams of deionized water. If the pH was below 6.5 0.2 gram increments of diethanolamine was added until the pH is between 6.5 and 7.5.

EXAMPLE 12

Preparation of 1,3-Bis(nonylphenoxy)-2-propanol-block-(propylene oxide)$_{10}$

To a 500 milliliter stainless steel Zipperclave was added 100.0 grams (0.202 moles) of 1,3-bis(nonylphenoxy)-2-propanol prepared in Example 1 along with 0.7 grams of potassium hydroxide. The vessel was attached to an automated unit and was heated to 50° C. The vessel was continuously purged with nitrogen for 15 minutes and was then heated to 100°C. where it was again continuously purged with nitrogen for another 15 minutes. The vessel was then heated to 140° C. and is given a series of 6 purges by pressuring the vessel up to 80 psi, and then venting. Once the venting process was completed, the vessel was pressured to 20 psi with nitrogen.

Lines connected to a cylinder which had been precharged with 117.0 grams of propylene oxide (2.02 moles) were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until all of the propylene oxide had been fed. After the feed was complete, the reaction was allowed to continue for 1 hour after which the vessel was cooled to 60° C., purged 4 times with nitrogen to 80 psi and was dumped to a container. The final product yield was 211 grams with a theoretical yield of 277 grams. The GPC molecular weight of the product was Mw=650 and the Mn=490 based on monodisperse polystyrene standards.

EXAMPLE 13

Preparation of 1,3-Bis(nonylphenoxy)-2-propanol-block-(propylene oxide)$_{10}$-block-(ethylene oxide)$_{10}$ To a 500 milliliter stainless steel Zipperclave was added 75.0 grams of the propoxylate prepared in Example 12 (0.070 moles) along with 0.3 grams of potassium hydroxide. The vessel was attached to an automated ethoxylation unit and was heated to 50° C. The vessel was continuously purged with nitrogen for 15 minutes and was then heated to 100° C. where it was again continuously purged with nitrogen for another 15 minutes. The vessel was then heated to 140° C. and was given a series of 6 purges by pressuring the vessel up to 80 psi, and then venting. Once the venting process was completed, the vessel was pressured to 20 psi with nitrogen.

The ethylene oxide lines were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until 30.7 grams ethylene oxide (0.696 moles) was added based on a difference weight of the feed cylinder. After the feed was complete, the reaction is allowed to continue for 1 hour after which the vessel was cooled to 60° C., purged 4 times with nitrogen to 80 psi and was dumped to a container. The final product yield was 99 grams with a theoretical yield of 106 grams.

EXAMPLE 14

Preparation of Bis(nonylphenoxy) Adduct of 1,4-Butanediol Diglycidyl Ether

To a five neck, two liter round bottom flask equipped with an addition funnel, thermometer, nitrogen dispersant tube, mechanical stirrer, and a decanting head with a water-cooled condenser were added 506.8 grams (2.30 mole) of nonylphenol and 350 milliliters of cyclohexane. The solution was heated to reflux, and 6.5 grams (1.3 weight percent based on nonylphenol) of potassium hydroxide in 15 milliliters of water was slowly added to the round bottom flask. After all the water was recovered in the decanting head (15 milliliters+2 milliliters formed), 220 grams (1.09 mole) of 1,4-butanediol diglycidyl ether was added dropwise between 60 and 80° C. After the addition was complete, the solution was refluxed for four hours. The contents of the flask were then washed with a five percent aqueous solution of phosphoric acid, and the organic layer was separated from the water layer and washed twice with deionized water. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180° C. during the distillation to prevent discoloration of the product. The concentrated solution was then refiltered to give 710 grams of a pale-yellow liquid. Molecular weight by end-group MW analysis was 689.9 (theoretical MW=643.0). Ir and nmr spectra were consistent with the expected structure of the product.

EXAMPLE 15

Preparation of 3 Mole Ethoxylate of 1,3-Bis(nonylphenoxy)-2-propanol

To a five hundred milliliter Zipperclave reactor were charged, under nitrogen, 200.1 grams (0.43 mole) of 1,3-bis(nonylphenoxy)-2-propanol prepared in Example 2 and 0.20 grams (0.1 weight percent) of $BF_3.Et_2O$. The reaction mixture was heated to 80° C., and 55.1 grams (1.25 mole) of ethylene oxide was fed to the reactor over a two hour period. After all the ethylene oxide was fed, the reaction mixture was allowed to cook out for one hour and then dumped hot, under nitrogen, into a jar containing 160 milliliters of a one percent aqueous solution of sodium hydroxide. The organic layer was separated from the water layer and washed twice with deionized water. The washes were performed at 90° C. to facilitate the separation of the two layers. The product was then dried by azeotropic removal of the water, using cyclohexane (300 milliliters) as the entrainer. The cyclohexane was stripped off under vacuum to give a pale-yellow liquid with a molecular weight by end-group MW analysis of 601.7 (theoretical MW=629). Ir and nmr spectra were consistent with the expected structure of the product.

EXAMPLE 16

Preparation of 8 Mole Ethoxylate of Bis (nonylphenoxy) Adduct of 1,4-Butanediol Diglycidyl Ether To a five hundred milliliter Zipperclave reactor were charged, under nitrogen, 150.2 grams (0.22 mole) of bis (nonylphenoxy) adduct of 1,4-butanediol diglycidyl ether prepared in Example 14 and 0.30 grams (0.2 weight percent) of $BF_3 \cdot Et_2O$. The reaction mixture was heated to 80° C., and 77.5 grams (1.76 mole) of ethylene oxide was fed to the reactor over a two hour period. After all the ethylene oxide was fed, the reaction mixture was allowed to cook out for one hour and then dumped hot, under nitrogen, into a jar containing 160 milliliters of a one percent aqueous solution of sodium hydroxide. The organic layer was separated from the water layer and washed twice with deionized water. The washes were performed at 90° C. to facilitate the separation of the two layers. The product was then dried by azeotropic removal of the water, using cyclohexane (300 milliliters) as the entrainer. The cyclohexane was stripped off under vacuum to give a pale-yellow liquid with a molecular weight by end-group MW analysis of 1047 (theoretical MW=995). Ir and nmr spectra were consistent with the expected structure of the product.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A compound represented by the formula:

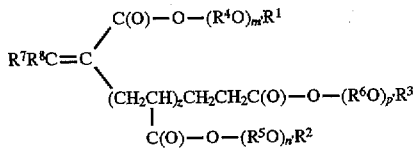

wherein $R^1$, $R^2$ and $R^3$ are the same or different and are hydrogen, a substituted or unsubstituted monovalent hydrocarbon residue or a monovalent residue of a substituted or unsubstituted complex hydrophobe compound, provided at least one of $R^1$, $R^2$ and $R^3$ is a monovalent residue of a substituted or unsubstituted complex hydrophobe compound;

m', n' and p' are the same or different and are a value of 0 or greater, provided that at least one of m', n', or p' is a value of at least 2;

z is a value of 0 or greater;

each $R^4$ is the same or different and is a substituted or unsubstituted divalent hydrocarbon residue;

each $R^5$ is the same or different and is a substituted or unsubstituted divalent hydrocarbon residue;

each $R^6$ is the same or different and is a substituted or unsubstituted divalent hydrocarbon residue; and $R^7$ and $R^8$ are the same or different and are hydrogen or a substituted or unsubstituted monovalent hydrocarbon residue; in which said substituted or unsubstituted complex hydrophobe compound is represented by the formula selected from:

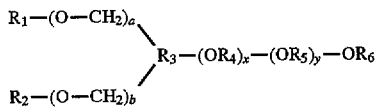

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$; and

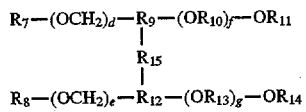

wherein $R_7$ and $R_8$ are the same or different and are hydrogen or a substituted or unsubstituted monovalent hydrocarbon residue, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are the same or different and are hydrogen a substituted or unsubstituted monovalent hydrocarbon residue or an ionic substituent, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ an $R_{14}$ or having greater than 2 pendant carbon atoms in the case of $R_9$, $R_{10}$, $R_{12}$, $R_{13}$ and $R_{15}$.

2. The compound of claim 1 wherein $R_1$, $R_2$, $R_7$ and $R_8$ are selected from substituted or unsubstituted alkyl, aryl, alkylaryl, arylalkyl, cycloalkyl or mixtures thereof.

3. The compound of claim 1 wherein $R_1$, $R_2$, $R_7$ and $R_8$ are selected from dodecylphenyl, nonylphenyl, octylphenyl or mixtures thereof.

4. The compound of claim 1 wherein at least one of $R_1$, $R_2$, $R_7$ and $R_8$ is a hydrocarbon radical represented by the formula:

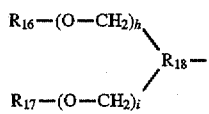

wherein $R_{16}$ and $R_{17}$ are the same or different and are hydrogen or a substituted or unsubstituted monovalent hydrocarbon residue, $R_{18}$ is a substituted or unsubstituted divalent or trivalent hydrocarbon residue, and h and i are the same or different and are a value of 0 or 1.

5. The compound of claim 1 wherein at least one of $R_4$, $R_5$, $R_{10}$ and $R_{13}$ is a hydrocarbon radical represented by the formula:

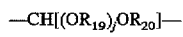

wherein each $R_{19}$ is the same or different and is a substituted or unsubstituted divalent hydrocarbon residue, $R_{20}$ is hydrogen, a substituted or unsubstituted monovalent hydrocarbon residue or an ionic substituent, and j is a value of 0 or greater.

6. The compound of claim 1 wherein each $R_4$, $R_5$, $R_{10}$ and $R_{13}$ is selected from —$CH_2CH_2$—, —$CH_2CH(CH_3)$— or mixtures thereof.

7. The compound of claim 1 wherein $R_6$, $R_{11}$ and $R_{14}$ are hydrogen.

8. The compound of claim 1 wherein the values of x, y, f and g are from 0 to about 200 or greater.

* * * * *